US006921637B2

(12) United States Patent
Audeh et al.

(10) Patent No.: US 6,921,637 B2
(45) Date of Patent: Jul. 26, 2005

(54) COLLOID COMPOSITIONS FOR SOLID PHASE BIOMOLECULAR ANALYTICAL, PREPARATIVE AND IDENTIFICATION SYSTEMS

(75) Inventors: Zuheir L. Audeh, Brookline, MA (US); Dolores A. Fici, Revere, MA (US); William McCormick, Concord, MA (US)

(73) Assignee: The CBR Institute for Biomedical Research, Inc., Boston, MA (US)

( * ) Notice: Subject to any disclaimer, the term of this patent is extended or adjusted under 35 U.S.C. 154(b) by 0 days.

(21) Appl. No.: 09/848,777

(22) Filed: May 4, 2001

(65) Prior Publication Data

US 2002/0015958 A1 Feb. 7, 2002

Related U.S. Application Data

(60) Provisional application No. 60/201,908, filed on May 4, 2000.

(51) Int. Cl.[7] ....................... G01N 33/53; G01N 33/543
(52) U.S. Cl. ............................... 435/6; 435/4; 435/7.1; 435/7.9; 435/7.92; 435/287.1; 436/164; 436/172; 436/518; 436/524; 436/532; 436/536; 422/68.1
(58) Field of Search ........................... 435/4, 6, 7.1, 7.9, 435/7.92, 287.1; 436/164, 172, 518, 524, 532, 536; 422/68.1

(56) References Cited

U.S. PATENT DOCUMENTS

| 5,122,600 A | * | 6/1992 | Kawaguchi et al. ....... 536/23.1 |
| 5,194,372 A | * | 3/1993 | Nagai et al. .................... 435/6 |
| 5,667,976 A | * | 9/1997 | Van Ness et al. ................ 435/6 |
| 5,744,305 A | | 4/1998 | Fodor et al. .................... 435/6 |
| 5,807,522 A | | 9/1998 | Brown et al. .................. 422/50 |
| 5,830,645 A | | 11/1998 | Pinkel et al. .................... 435/6 |
| 5,837,196 A | | 11/1998 | Pinkel et al. ................. 422/55 |
| 5,856,092 A | * | 1/1999 | Dale et al. ....................... 435/6 |
| 6,033,853 A | * | 3/2000 | Delair et al. .................... 435/6 |
| 6,110,426 A | | 8/2000 | Shalon et al. .............. 422/68.1 |
| 6,110,464 A | * | 8/2000 | Malvar et al. ............ 424/185.1 |
| 6,114,115 A | * | 9/2000 | Wagner, Jr. ..................... 435/6 |
| 6,146,593 A | | 11/2000 | Pinkel et al. ............... 422/68.1 |
| 6,159,685 A | | 12/2000 | Pinkel et al. ................ 435/6 |
| 6,197,599 B1 | | 3/2001 | Chin et al. .................. 436/518 |
| 6,391,569 B1 | * | 5/2002 | Grieve et al. ............. 435/7.22 |
| 6,468,811 B1 | * | 10/2002 | Seul ............................ 436/535 |

FOREIGN PATENT DOCUMENTS

| WO | WO 94/26933 | 11/1994 | ............ C12Q/1/68 |
| WO | WO 97/40385 | 10/1997 | |
| WO | WO 98/20353 | 5/1998 | ......... G01N/33/567 |
| WO | WO 99/07892 | 1/1999 | ............ C12Q/1/68 |
| WO | WO 00/00808 | 1/2000 | |
| WO | WO 00/03037 | 1/2000 | ............ C12Q/1/68 |

OTHER PUBLICATIONS

US 6,066,453, 5/2000, Pinkel et al. (withdrawn)

Susan B. Yox, RN, EdD, "The Laboratory on a Chip—The Future of Miniaturization and Automation", Laboratory Medicine, vol. 30, No. 7, pp. 456–461 (1999).

Pinkel et al., "High Resolution Analysis of DNA Copy Number Variation Using Comparative Genomic Hybridization to Microarrays", Nature Genetics, vol. 20, pp. 207–211 (1998).

MacBeath et al., "Printing Proteins as Microarrays for High–Throughput Function Determination", Science, vol. 289, pp. 1760–1763 (2000).

Lemieux et al., "Overview of DNA chip technology", Molecular Breeding, vol. 4, pp. 277–289 (1998).

Eric S. Lander, "Array of Hope", Nature Genetics Supplement, vol. 21, pp. 3–61 (1999).

Haab et al., "Protein Microarrays for Highly Parallel Detection and Quantitation of Specific Proteins and Antibodies in Complex Solutions", vol. 2 No. 2, 13 Pages, http://genombiology.com (2001).

Guo et al., "Oligonucleotide Arrays for High Resolution HLA Typing", Reviews in Immunogenetics, vol. 1, pp. 220–230 (1999).

Grace Bio–Labs, "ONCYTE Film–Slides", "HybriWell Sealing System", "HybriSlip Hybridization Covers", "MultiWell Press–to–Seal Arrays", "Grace Bio–Labs–About Grace", "What's New In Our Laboratory", www.gracebio.com (1998).

Mary Jane Friedrich, "New Chip on the Block—The Arrival of Biochip Technology", Laboratory Medicine, vol. 30, pp. 179–188 (1999).

Unknown Author, "Microarray Configuration Formats", Slide show. (1999).

William J. Cromie, "Identifying Source of Disease–Faulty Proteins Account for Most of the World's Sickness", Harvard University Gazette, vol. XCVI, No. 3, pp. 1and 4 (2000).

* cited by examiner

Primary Examiner—Chris Chin
Assistant Examiner—Kartic Padmanabhan
(74) Attorney, Agent, or Firm—William G. Gosz; Fish & Neave IP Group Ropes & Gray

(57) ABSTRACT

A liquid composition comprising a colloidal suspension of a biomolecule-binding matrix material (preferably nitrocellulose) dispersed in a liquid, with particles of the matrix material being of a defined particle size, and replicate copies of a biomolecule, e.g., protein or nucleic acid probes, which are distributed, preferably uniformly, throughout the colloidal suspension and are bound to the matrix material particles, is disclosed. The liquid composition of the invention can be used directly for sample analysis or preparation of biomolecules, or aliquots of the composition can be spotted onto a support to form a microporous matrix system or microarray for analysis or preparation of biomolecules. Compositions and microarrays according to the invention are useful in any type of analytical or preparative procedure relating to biomolecules. They are particularly useful, e.g., in methods for detecting a biomolecule analyte in a liquid sample, methods for determining the presence of a particular nucleic acid sequence within a liquid sample and methods for determining the presence of a drug candidate molecule in a liquid sample. The invention further comprises kits for practicing the various methods of the invention.

13 Claims, 5 Drawing Sheets

Micrograph scan of colloidal particles less than 45 μm in diameter

Colloid is labeled with fast green dye and scanned using a red laser

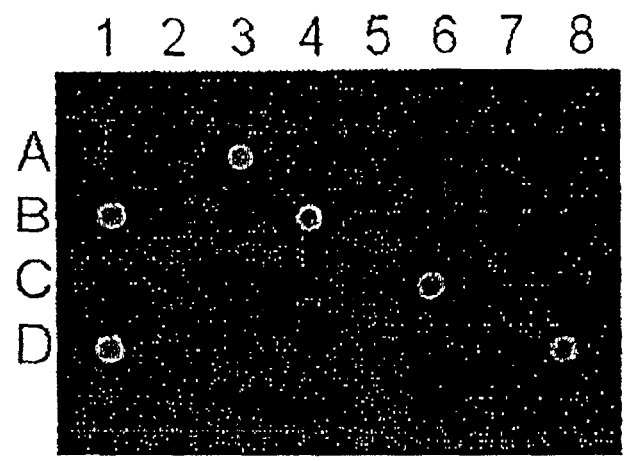
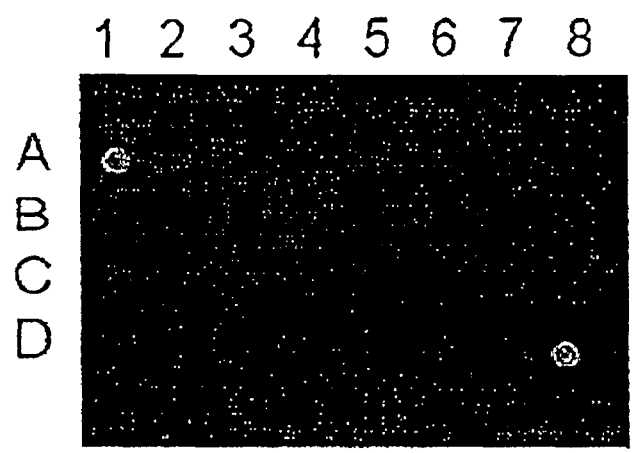
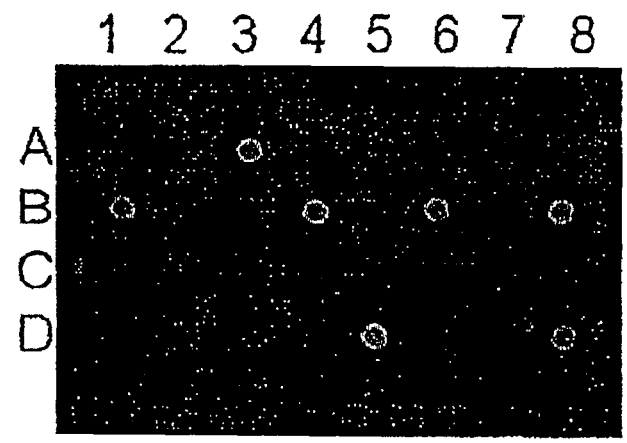
Fig. 4

COLLOID COMPOSITIONS FOR SOLID PHASE BIOMOLECULAR ANALYTICAL, PREPARATIVE AND IDENTIFICATION SYSTEMS

CROSS REFERENCE TO RELATED APPLICATIONS

This application claims the priority of U.S. Provisional Application No. 60/201,908 filed May 4, 2000 entitled, NOVEL COLLOID COMPOSITIONS USEFUL IN THE PREPARATION OF SOLID PHASE BIOMOLECULAR ANALYTICAL PREPARATIVE AND IDENTIFICATION SYSTEMS, the whole of which is hereby incorporated by reference herein.

STATEMENT REGARDING FEDERALLY SPONSORED RESEARCH OR DEVELOPMENT

Part of the work leading to this invention was carried out with United States Government support provided under a grant from the National Institutes of Health, Grant No. 1R43CA80579-01. Therefore, the U.S. Government has certain rights in this invention.

BACKGROUND OF THE INVENTION

Various polymer-based, solid support and/or porous matrix systems are in common use in molecular biology research, genetic analysis and diagnosis. In these systems, a biopolymer, such as a specific antibody or a nucleic acid for an antigen-antibody binding determination or a nucleic acid hybridization analysis, respectively, is used as an analytical probe and affixed, e.g., to a porous matrix which may be layered on a solid support. The material of a porous matrix commonly consists of a highly charged polymer such as nitrocellulose, activated nylon, polyvinyl difluoride (PVDF) or agarose beads as shown in Chin et al., U.S. Pat. No. 6,197,599. In other such biopolymer probe systems used for microarray analysis, for example U.S. Pat. No. 5,744,305 (Fodor et al.), the probe of interest is chemically reacted with a solid surface and a biopolymer probe-binding matrix, such as nitrocellulose, is not required.

Such systems are used, e.g., to identify or isolate molecular species contained within a biological preparation to be characterized. The species of interest hybridizes or binds to the target biopolymer probes, which are provided in a solid support form, such as in a glass or plastic slide configuration.

Microarray technology is a recent application of hybridization based approaches to analysis of nucleic acids (DNA, cDNA, and RNA) in biological samples. This technology is basically a miniaturization of the well-known membrane hybridization technology introduced by Southern and others in the 1970's. In this technology, small volumes of different oligonucleotides or PCR-DNA or cDNA samples are spotted or synthesized on a membrane or a solid surface at very high densities to form a single microarray. Each spot within the array contains replicate copies of a single nucleic acid probe species ($NA_x$, wherein x varies according to the base sequence composition of the nucleic acid) and the array consists of a multiplicity of spots encompassing a collection of different species ($NA_{x1}$, $NA_{x2}$, ...), each of which is in a known position in the spotted array. Such a microarray can be hybridized to an unknown nucleic acid sample to determine the degree of complementarily between the the individual nucleic acids in the unknown sample and the different, known nucleic acid species on the microarray.

Preparation of microarray systems of the prior art is a very labor intensive endeavor, however. It would be desirable to have additional ways to prepare such systems that would require fewer steps on the part of the end user and that would result in the reduction or elimination of process-related variability from laboratory to laboratory.

BRIEF SUMMARY OF THE INVENTION

The compositions, systems and methods of the invention provide the desired improvements over the prior art. In one aspect, the invention is directed to a liquid composition comprising a colloidal suspension of a biomolecule-binding matrix material dispersed in a liquid, with particles of the matrix material being of a defined particle size, and replicate copies of a biomolecule, which are distributed, preferably uniformly, throughout the colloidal suspension and are bound to the matrix material particles. The matrix material, preferably, is nitrocellulose, polyvinyl difluoride or activated nylon, and the biomolecule, preferably, is a biopolymer, most preferably a nucleic acid or a protein.

The liquid composition of the invention can be used directly for sample analysis or preparation of biomolecules, or aliquots of the composition can be spotted onto a support to form a microporous matrix system or microarray for analysis or preparation of biomolecules. Aliquots of the liquid composition of the invention can also be dried to produce a powder of microfine particles (e.g., having diameters of less than 10 $\mu$m and preferably 100–500 nm). This powder can be applied to a solid support in a microarray pattern, e.g., by electrostatic printing, also to form a microarray of the invention.

Compositions and microarrays according to the invention are useful in any type of analytical or preparative procedure relating to biomolecules. They are particularly useful, e.g., in methods for detecting a biomolecule analyte in a liquid sample, methods for determining the presence of a particular nucleic acid sequence within a liquid sample and methods for determining the presence of a drug candidate molecule in a liquid sample. Drug candidates identified using the methods of the invention are also within the scope of the invention. The invention further comprises kits for practicing the various methods of the invention. For example, a useful kit would include a particular microarray according to the invention, and reagents and instructions for practicing the specific method identified, the reagents being packaged in a convenient easy-to-use format.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 1A is a drawing of a microscope slide having thereon a colloidal microarray according to the invention;

FIG. 1B is an exploded view of a typical spot of the microarray of FIG. 1A showing that the spot is composed of a large number of colloidal particles of the matrix biomolecule;

FIG. 1C is an exploded view of a single colloidal particle of FIG. 1B showing the particle coated with antigen;

FIG. 1D is an exploded view of the single colloidal particle of FIG. 1C showing a bound antigen probe;

FIG. 1E shows the antigen probe molecule of FIG. 1D after binding to a specific antibody present in a test sample;

FIG. 1F shows the antigen/antibody combination of FIG. 1E bound to a detector fluorophore. The intensity of the fluorophore signal is used as a measure for the level of different antibodies in the test sample;

FIG. 4 is a micrograph of three microarrays according to the invention showing the results of HLA typing of three different individuals.

DETAILED DESCRIPTION OF THE INVENTION

Figure 1:
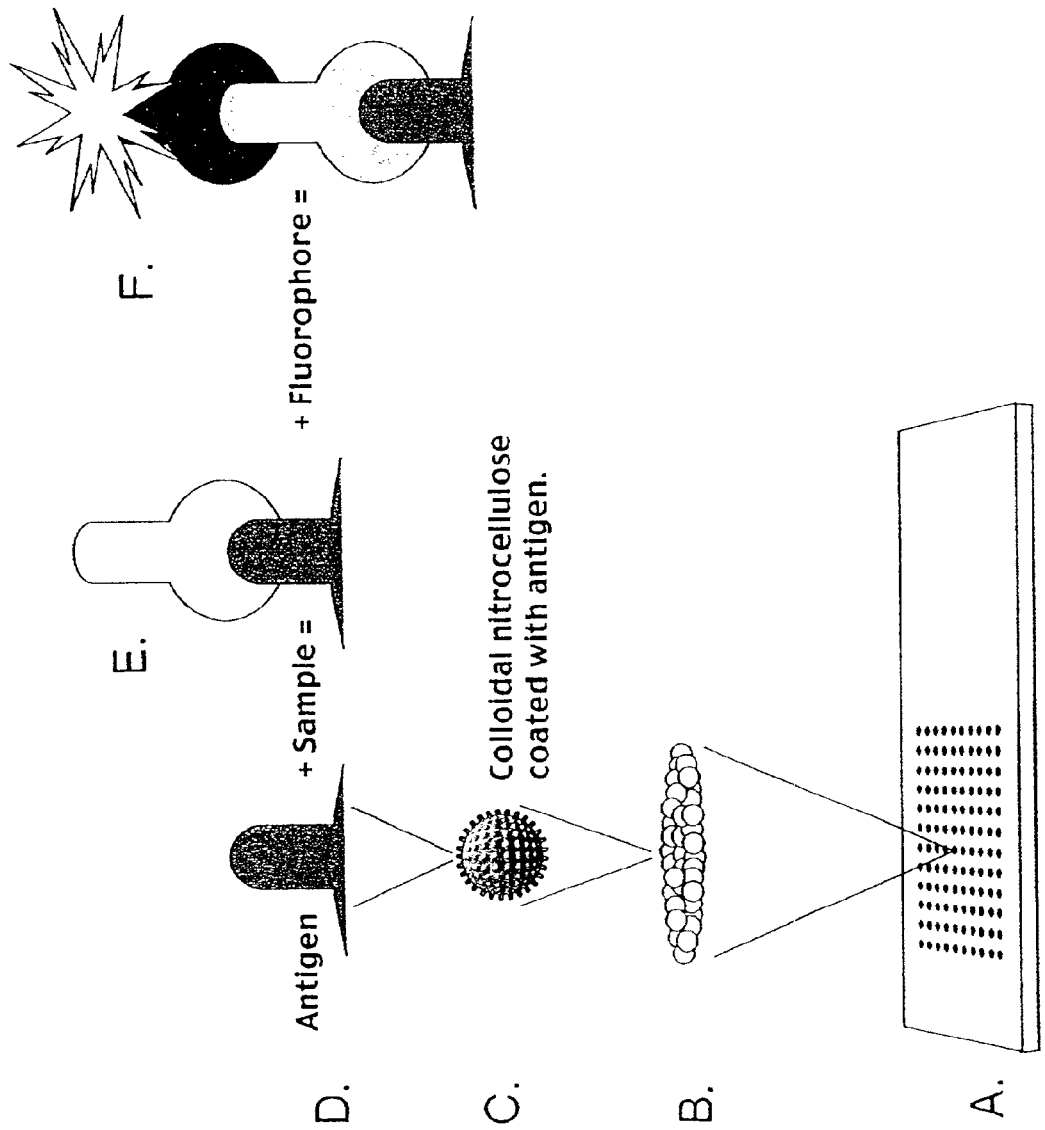
FIGS. 1A–1F show the components and principle of use of a microarray according to the invention, specifically.

This invention relates to new liquid colloid-based compositions containing biomolecules, e.g., proteins, nucleic acids, or other biopolymers of interest, bound to particles of a matrix material. The compositions of the invention are useful in the preparation of solid support, polymer-based, porous matrix analytical or preparative systems for identification, isolation, detection, characterization and/or analysis of biological specimens, which specimens may contain species of biomolecules (targets) that specifically bind to or associate with the biomolecules, or probes, in the composition. In two particular embodiments, the invention is directed to systems for nucleic acid or protein characterization and specifically to the means and methods for preparing analytical or chromatographic/preparative systems such as analytical nucleic acid or protein-based microarrays or preparative affinity-based separation materials, respectively.

In prior art systems, probes are deposited on a solid support, e.g., in the pattern of a microarray and, subsequently, cross-linking and blocking steps are carried out on the preformed probe/solid porous matrix complex within the microarray as part of an analytical procedure. In the prior art, the solid matrix is prepared at the point of manufacture, usually in a slide or membrane format. At the end user level, the probe is then added. The assembly process continues with the cross-linking of the probe within the polymer matrix and then the reduction of non-specific background binding by blocking out with non-specific nucleic acids and/or proteins to cover sites within the polymer matrix to which the probe is not bound.

In the system of the invention, however, the probe is added to the colloid-based matrix material in liquid composition format before the composition is spotted on a solid support. Moreover, cross-linking and blocking steps may be carried out either before or after the probe biopolymer-containing solid matrix is formed. This flexibility provides the opportunity of performing these steps at the point of manufacture rather than at the end-user laboratory stage of product use. It is well known that the cross-linking and blocking steps in the laboratory are associated with both time-consuming sample processing and great variability in final results from run to run within a given laboratory and between laboratories. Of particular importance is that the failure to block out non-specific binding sites of the matrix may contribute to background signals that adversely effect analytical discrimination between probe-specific and non-probe/non-specific binding. These variations in prior art systems lead to undesirable disparities of results among different analyses of the same unknowns.

Thus, an advantage of this invention is to provide for the bulk spotting of microarrays and the elimination of process-related variations by preparing the analytical systems, such as nucleic acid microarrays, with cross-linking and blocking steps all to be carried out at the manufacturing level. Thus, uniform quality control of the microarray slides at the point of manufacture is possible so that each spot contains a specific crosslinked and background-blocked probe. This allows different laboratories to conduct analyses with replicate probe-solid support systems of probes without the time-consuming and error-related cross-linking and blocking steps.

The system of the invention has utility, e.g., for oligonucleotides, full length cDNAs and oligopeptides, as well as for large full length proteins, i.e., any biopolymer that can be made to carry a charge. For this reason, it offers the advantage of greater versatility in preparing microarrays for more applications than can be provided by prior art microarray systems, which are prepared with de novo synthesis of the respective nucleic acid/biopolymers for each spot.

For the purposes of illustrating some of the advantages of this invention, its use is described particularly in the preparation and use of DNA and protein microarrays. However, as will become obvious to those skilled in the art, comparable advantages and benefits will be apparent in the use of the liquid compositions of this invention to prepare other solid support systems such as in high surface area affinity-based separation methods or analyses. In a further aspect of this invention, the liquid colloid-based compositions of the invention are used directly to facilitate separation processes, e.g., isolation or detection systems, carried out under liquid or fluid conditions. For example, liquid polymer-based compositions of the invention could be used in a slurry form for contacting and allowing the binding of compounds from a sample of interest, and then polymer matrix-based fractions could be centrifuged out and washed. The bound selected species of interest could then be isolated from the matrix material. Alternatively, polymer matrix-based material can be formed as a packing material for an affinity chromatographic-type column in analytical and/or preparative procedures.

Thus, in certain preferred embodiments, the invention provides for a novel composition useful in the preparation of nucleic acid or protein microarrays on solid supports, e.g., glass or plastic microscope slides. Preferred embodiments of the composition of the invention contain at least the following three components: (i)replicate copies of, e.g., a nucleic acid fragment (oligonucleotide or full length cDNA); (ii) a polymer composition, such as nitrocellulose, that is capable of forming a generally porous molecular matrix and of binding to the nucleic acid; and (iii) a liquid within which polymer molecules and bound nucleic acid probes are uniformly dispersed in colloidal suspension.

Preferably, the composition also includes, as a fourth component, blocking reagents such as protein or non-specific DNA, which are added after the nucleic acid and polymer are equilibrated in the desired proportions. Most preferably, the blocking reagents occupy all non-specific binding sites so that only the probe, e.g., single stranded nucleic acid, is available for binding to material in a sample to be tested. The ratio of the concentrations of the nucleic acid and polymer in the composition are preferably predetermined so as to obtain a desired hybridization condition and/or to optimize the signal desired in final analytical analysis. This ratio may also be optimized to provide the maximum amount of nucleic acid probe and a minimum amount of polymer matrix.

The composition of the invention makes possible a method of making a nucleic acid microarray wherein each different spot, which individually contains replicates of a given probe species, $NA_x$, is derived from a common liquid composition preparation so that there is no variation from spot to spot. Furthermore, using the composition of the invention, it is possible to make a nucleic acid microarray wherein each spot has a specifically determined concentration of oligonucleotide and wherein the actual molar concentration of the oligo or cDNA species for the respective spots of the microarray may not be equal in order to optimize the characteristics of the entire array to obtain certain desired performance parameters, e.g., a uniform analytical signal among the spots, in order to achieve a desired uniformity in hybridization temperature conditions.

The ratio of the concentration of oligonucleotide probe to the concentration of polymer matrix material is established so that the analytical signal of positive hybrids can be optimized by minimizing the amount of polymer present. Thus, a microarray can be prepared in which the amount of polymer may be varied as desired from spot to spot, e.g., the amounts of polymer for spots of a given $NA_x$ species are equal, but the amount of polymer for spots of different species ($NA_{x1}$ and $NA_{x2}$) could be different. Spotting compositions according to the invention can be prepared so that certain conditions for use of the resulting microarray, e.g., hybridization melt temperature, may be selected in part by including an additional component or by carrying out a physical or chemical treatment of the spotting composition. Thus, the microarray designer is provided with a variable composition parameter wherein hybridization conditions can be adjusted by something other than the base composition of the oligonucleotide.

The following examples are presented to illustrate the advantages of the present invention and to assist one of ordinary skill in making and using the same. These examples are not intended in any way otherwise to limit the scope of the disclosure.

EXAMPLE I

Preparation of a Generic Composition According to the Invention and use of the Composition for Preparation of a Microarray The first step in implementing the improvements possible with assay systems according to the invention is to prepare a colloidal suspension of defined particle size matrix material from, e.g., a highly charged material such as nitrocellulose, activated nylon or polyvinylidene difluoride. These materials are capable of binding or adsorbing a variety of charged molecules such as nucleic acids, proteins, etc., and such binding is sufficiently strong to survive the high stringency conditions required for hybridization reactions. The matrix material in colloidal suspension could also be a non-charged polymer, such as plastic, nylon or polysulfone. The colloids are prepared by using any number of traditional methods that may include pulverization, precipitation and spray drying, as well as a variety of other well-established techniques.

To aliquots of this stable colloidal suspension in water (or buffer) are added replicate copies of individual probes. The substrate probe of interest can be bound by ionic and non-ionic as well as covalent and non-covalent bonds to the matrix material. These substrates include but are not limited to proteins, glycoproteins, polysaccharides, peptides, hormones, vitamins, drugs, single or double stranded DNA, RNA, and oligonucleotides. Individual substrates or combinations of different substrates are mixed with the colloid suspension and incubated for at least one hour at room temperature in appropriate solution.

Then, binding sites on the highly charged matrix material not occupied by molecules of the probe can be blocked with any of the known blocking agents. To assure complete saturation of the binding sites on the surface of the colloidal particles, a blocking step is required, and the colloid/substrate mixture is incubated with excess blocking solution, which may contain non-specific proteins such as milk or non-specific DNA such as salmon sperm DNA. At this stage the colloid/substrate preparation can be stored for extended periods of time.

The desired number of probe-containing (and preferably blocked) liquid compositions are spotted on a solid support (e.g., a slide, porous bead or flexible tape made, e.g., from glass, plastic or polycarbonate) and are allowed to dry and bind to the support. The support can have any physical or chemical surface modification appropriate for the intended use. For example, a flat surface can be modified to include wells, protrusions, or channels. Individually prepared solid supports, e.g., microscope slides, are then used, e.g., in a reverse sequence-specific oligonucleotide probe hybridization protocol or for the determination of ligand/protein interactions.

The novel probe-treated and blocked colloidal suspensions are also useful separately, e.g., to isolate specific sequence-containing nucleic acids that hybridize to the attached nucleic acid probe of interest. For example, a probe-containing emulsion or colloid can be exposed to a sample with a mixture of heterogeneous nucleic acid and then centrifuged and washed. The isolated nucleic acid is then removed from the attached probe, e.g., by heating.

Specifically, in a typical reverse sequence-specific oligonucleotide probe hybridization protocol array preparation according to the invention, nitrocellulose powder (e.g., from Aldrich Chemical Co.) is dissolved in an organic solvent such as acetone or in a mixture of organic solvents such as acetone-butanol-ethanol, etc. The clear nitrocellulose solution is added to a large volume of a polar solvent, such as water, in such a way that a major fraction of the dissolved nitrocellulose forms a milky colloidal suspension of nitrocellulose, e.g, with heating and continuous mixing. The polymer in this solution precipitates out of the water/organic mixture in a colloidal form. This colloid is either filtered through a specific pore size membrane (e.g., standard Nalgene or Millipore filter units having pore diameters of 0.20–0.45 $\mu$m) or centrifuged and re-suspended in a buffer such as 3×SSC, at a final concentration of 10%–50% nitrocellulose. Typically, a preparation containing nitrocellulose at concentrations ranging from 10 to 40% (v/v) in aqueous solution yields colloidal particles having diameters ranging from approximately 0.2 to 0.4 $\mu$m. The precipitated or filter-collected colloidal particles may be treated to improve their utility by acid contact or acid washing (e.g., with nitric acid). The colloidal particles are then washed free of acid and resuspended in an aqueous medium.

An aqueous preparation of the biopolymer or biomolecule probe of interest is then provided. This preparation may also contain other components. For example, a known concentration of a reference chromophore or dye material, such as Fast Green (Amresco), having an optical detection wavelength different from that of the fluorophore-labeled biomolecule analyte to be detected may be included. Such a reference chromophore would serve as a detection marker to determine the quantity of probe biomolecule deposited in a specific spot of a microarray, as may be useful for manufacturing quality control purposes. This dye marker could also serve as a reference internal standard for quantitating the optical signal of the fluorophore-labeled biomolecule analyte bound to a specific probe in microarray analysis. In a similar manner, a different dye marker could be added to the colloidal preparation before biopolymer addition and used to track the concentration of matrix material from the colloidal preparation through the various preparative procedures.

Different aliquots of the colloidal preparation are then each combined with a known quantity of a solution of a specific probe, and the combined solutions are allowed to incubate so that the biomolecule probe binds to the surfaces of the colloidal particles. For nucleic acid assays, the bound nucleic acid probes are preferably then "crosslinked" to the nitrocellulose matrix particles. In this context, "crosslinking" means exposing the colloidal suspension to, e.g., UV light or heat. This treatment causes the probe to lose tertiary structure and bind non-covalently to the highly charged polymer matrix support.

After the probes have been allowed to bind to the colloidal particles, blocking may be carried out to completely saturate the unoccupied binding sites of the colloidal particles with, e.g., non-specific DNA and/or protein as appropriate. After this blocking incubation, it may be desirable to wash the preparation to remove excess probe and blocking reagents.

Following the blocking step, other components may be added to the particle/probe preparation. For example, it may be desirable to add a surfactant to the preparation for the purpose of enhancing the deposition of the particle/probe liquid solution onto solid support surfaces such as glass or plastic slides. Surfactants could include Tween 40, detergents or the like. Only those surfactants that would not be expected to interfere with the assay procedures would be selected. In addition, agents to promote the adhesion of the colloidal particles to a solid support surface could also be included.

The colloidal particle/probe samples were then placed in individual wells of a 96 well microtiter plate, and the samples were spotted using a GMS 417 Arrayer equipped with a 4-pin head. A single loading of the ring used to produce up to 400 spots per pin on the surface of a glass microscope slide. Arraying was carried out at room temperature, in a constant humidity environment, with the instrument protected from dust. The instrument in its actual operating mode washed each pin with water and ethanol and air dried the pins inbetween acquiring each different oligonucleotide sample. Array spots were placed at a center to center spacing of 300 μm. The identity and location of the oligonucleotide spots were tracked by computer.

Figure 2:
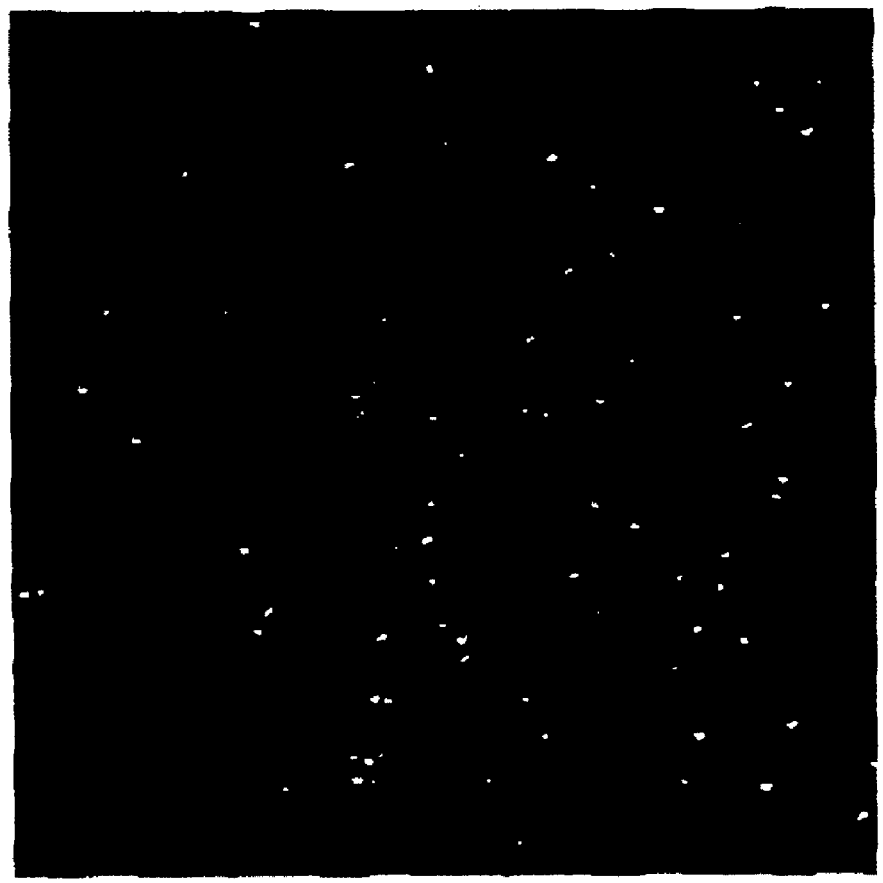
FIG. 2 is a micrograph scan of colloidal particles, such as in FIG. 1C, less than 45 μm in diameter.

The slides were allowed to dry at room temperature and then incubated in a sealed chamber containing a binding solution, such as 10–30%(V/V) acetone in water. Exposure to vapor of such a binding solution ensures proper adhesion of the spotted composition to the solid support as well as solidification of the composition of the spot. Referring to FIGS. 1A–1F, a representation of the make-up of an individual spot in an array, it can be seen in enlargement drawing FIG. 1B that, as a result of this incubation, the particles of nitrocellulose in the colloid bind to each other and to the solid support while still retaining their particular binding properties. The bound particles as a group form a porous structure so that the surfaces of the individual particles of nitrocellulose are exposed. A micrograph scan of colloidal particles according to the invention is shown in FIG. 2.

Following the blocking step, the slides are heated in an oven to dry and are ready to be used. For example, in a determination of the genotypes of unknown samples, each slide containing an array of spots of different $NA_x$ could be hybridized to an unknown nucleic acid sample to determine the degree of base complementarity between the sample and any of the characterized probe spots on the slide. For the HLA typing example described in Example III, thirty-two sequence specific oligonucleotide probes were used to assign intermediate level resolution HLA-DRB1 alleles.

EXAMPLE II

Determination of Protein/Ligand Interactions

Binding reactions between proteins and ligands can be evaluated easily using the system of the invention, e.g., as a means of obtaining useful information for diagnostic or research purposes. Furthermore, in drug discovery and development, the measured ligand/protein interactions can be determined in the presence of potential inhibitors or enhancers of selected protein/ligand binding. Specifically, e.g., antigen, for example, hepatitis B surface antigen, tetanus toxoid or viral antigens can be bound to the colloid matrix particles and used to detect specific antibody. Also, specific antibody can be bound to colloid to detect antigen.

In one embodiment, a spotting composition is prepared according to Example I to include a protein of interest or a segment thereof, that contains a ligand binding site. The composition is then treated with non-specific blocking agents, as in Example I. Microarray spotted slides are formed by deposition of very small, well defined amounts of the preparation on a suitable solid such as a glass or plastic slide. Such microarrays can contain a variety of concentrations of the protein of interest as well as internal controls such as proteins of various degrees of amino acid sequence variation.

Under suitable incubation conditions, the protein binding assay microarray slide can be incubated first with a mixture of ligands that might potentially bind to the proteins of the microarray. Chemical or physical conditions of incubation could be selected to eliminate non-specific binding and to establish a minimum binding energy threshold in order to select or detect ligands with a predetermined specificity and strength of binding to the protein probe in the microarray. Furthermore, a large number of different colloid/substrate preparations can be spotted in a microarray format and the presence or absence of a very large number of ligands present in a single sample can be determined simultaneously.

An assay is then carried out to identify those microarray spots in which significant binding has occurred. One technique is to contact the microarray slide a second time with an optically labeled ligand of well characterized binding properties. In the absence of a binding ligand in the mixture of unknowns, the labeled ligand would bind to the protein of interest. This binding can be detected by a suitably designed optical scanner. On the other hand, the absence of or reduction of signal intensity of the known ligand would indicate the presence of a potential binding ligand in the mixture of unknowns to be assayed.

Such a protein microarray would be applicable in evaluating, e.g., antibody/antigen interactions, adhesion molecule/ligand binding or enzyme/substrate interaction and the like. In addition, non-optical assays involving radiometric determinations could be employed in some cases, in combination with well known radioautoradiographic analytical methods to assay binding.

EXAMPLE III

HLA Typing

Figure 3:
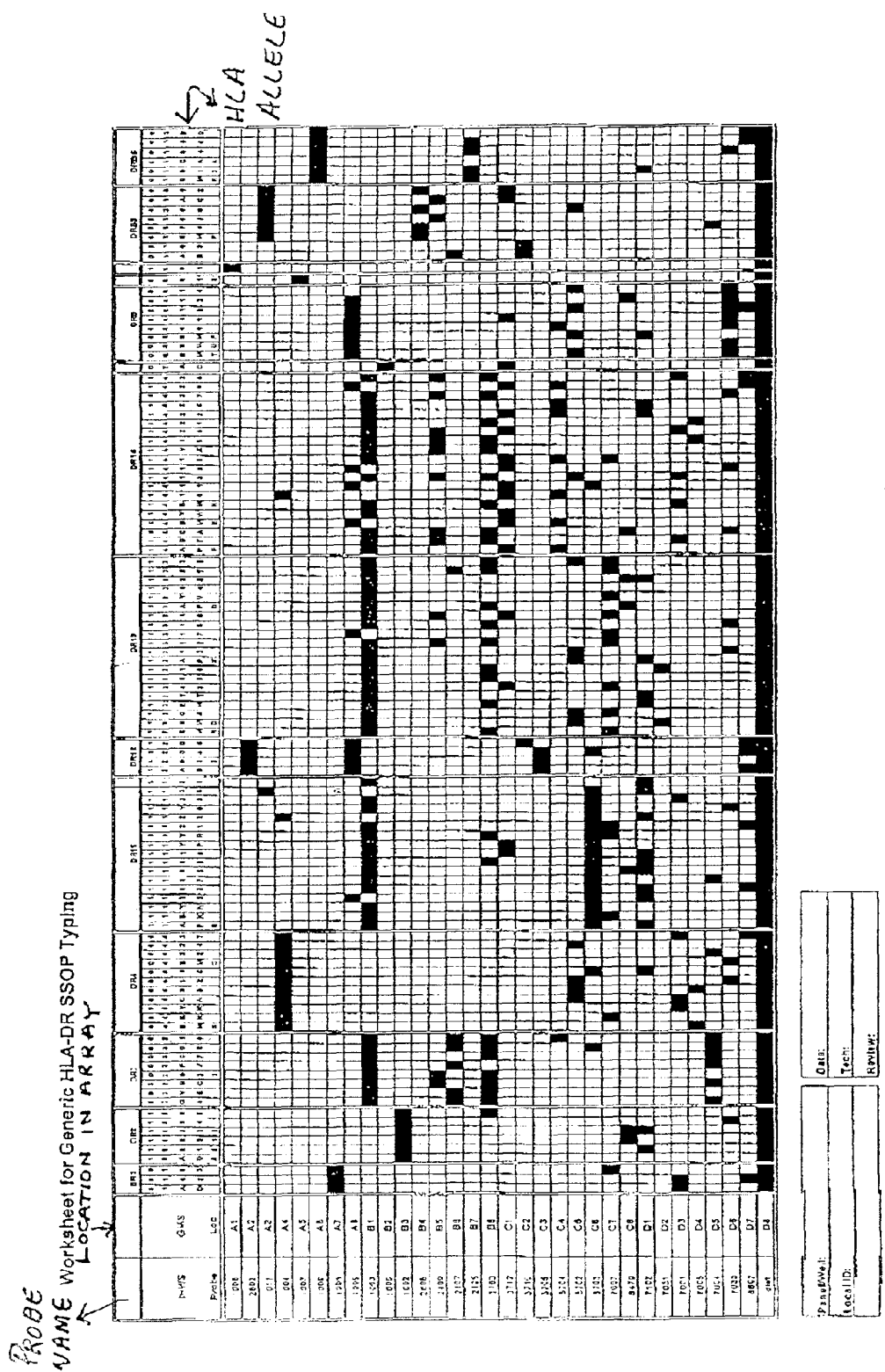
FIG. 3 is a worksheet for generic HLA-DR SSOP typing.

Although the membrane based system of the prior art has been a useful research tool and has been used for routine human leukocyte antigen (HLA) typing analysis, it is a cumbersome, manual procedure that is labor intensive and inefficient. Using the system of the invention, however, a much more convenient method for routine HLA typing can be devised. The new method comprises conventional isolation of genomic DNA from an individual and amplification of the HLA gene of interest using specific HLA primers. In addition, an HLA microarray can be made with each spot being formed from a liquid colloidal composition according to this invention, wherein the probe of each spot is a sequence specific oligonucleotide that is complementary to a region of a known HLA polynucleotide sequence. A plurality of such probes representing a plurality of the hypervariable regions were used. For example, for intermediate level resolution HLA-DRB1 typing, 32 probes, characterized in a "Worksheet for Generic HLA-DR SSOP Typing," shown in FIG. 3, were used to assign DRB1 alleles. Hybridizing the single stranded or denatured HLA PCR amplicon from an individual with the probes spotted will produce distinct patterns wherein only probes having complementarity with the single stranded DNA will hybridize. Labelling the hybridized single stranded HLA amplicon with an optical or other detectable label allows the analysis and interpretation to be fully automated based on the comparison of the pattern of positive signals. Referring to FIG. 4, the results of HLA typing of three different individuals are shown. The specific hybridization pattern for each individual can be located on the worksheet shown in FIG. 3 and the HLA alleles determined.

EXAMPLE IV

A Protein Target Microarray

Protein microarrays were prepared by binding to a nitrocellulose colloidal suspension each of the following antigens: hepatitis B surface antigen (HBsAg), tetanus toxoid, rubeola(measles), Varicella-Zoster virus (VZV), diphtheria, human cytomegalovirus (HCMV), and *Helicobacter pylori* (*H. pilori*). The binding was carried out by incubating three different dilutions of each of the antigens with a colloidal suspension for one hour at room temperature, at pH 7.4. The amount of antigen varied from 2 µg to 10 µg per 10 mg nitrocellulose colloid. A non-specific protein, e.g., 5% milk protein or 5% bovine serum albumin, was added to the colloid/antigen mixture and incubated for several hours to block the remaining free binding sites. A spotting microarrayer was used to spot 3 nl each of the blocked colloid/antigen mixture on a glass microscope slide.

To test for the presence of antibodies for these antigens in human serum samples, a number of test serum samples were diluted in blocking solution, added to the slide and incubated at room temperature for at least one hour. After this incubation, the slides were washed at room temperature with phosphate buffered saline (PBS) containing 0.5% Tween 20 and 2× with PBS containing 0.5% Tween 20 and 0.1% milk protein.

To detect for the presence of bound human antibody to each of the microspots in the array, a secondary antibody, e.g., anti-human IgG that was fluorescently labeled with Cy3, was then added to the slide and incubated at room temperature for one hour. The slide was then washed in PBS containing 0.5% Tween 20 and scanned using a laser scanner (Affymetrix 418). To determine the amount of human antibody bound to each of the antigens tested on the array, the fluorescence intensity level for each spot was measured and compared to the negative and positive control spots on the slide.

Figure 5:
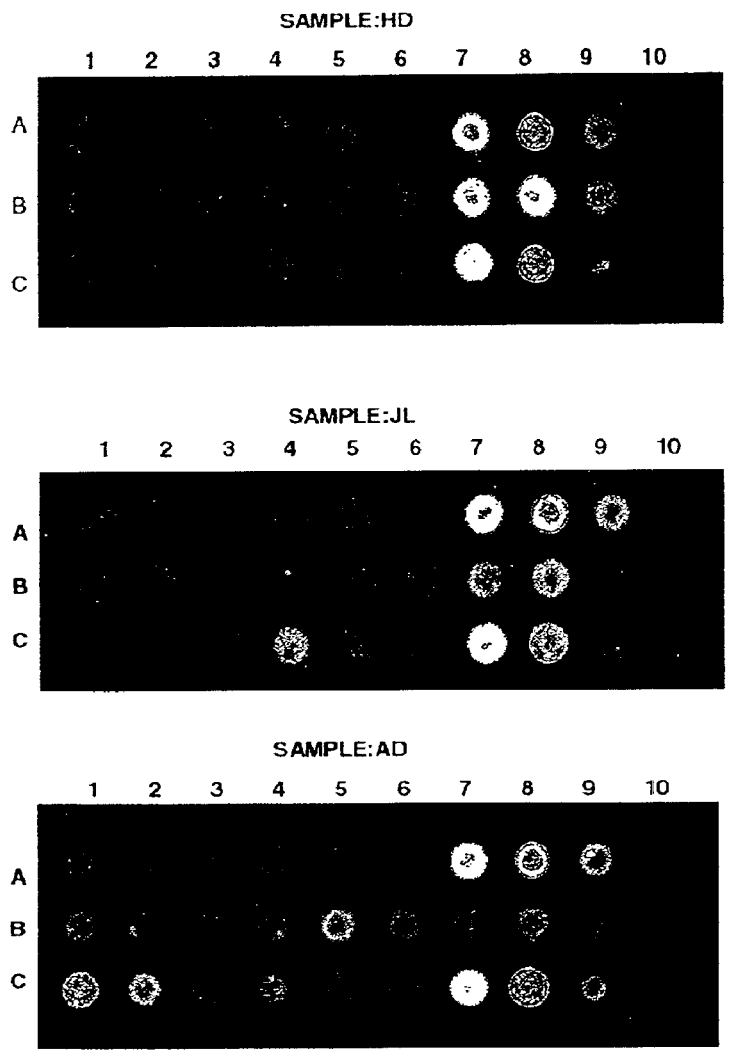
FIG. 5 is a micrograph of three microarrays according to the invention showing antibody profiles against a variety of antigens for three different individuals.

Examples of the antibody profile for these antigens from the sera of three individuals are shown in FIG. 5.

EXAMPLE V

Reduction in Background Fluorescence

Another advantage of using colloidal nitrocellulose for the preparation of microarrays is that the background non-specific fluorescence of the resulting microarray is significantly lower than that of the current commercially available slides coated with a layer of nitrocellulose as in the prior art. According to prior art methods, the nucleic acid analyte of interest, which is to be detected by hybridization to a nucleic acid probe, includes an optically detectable fluorophore or fluorescent molecule. This labeled analyte is added as a marker to a biological sample believed to contain the analyte of interest. After incubation of the biological sample with the microarray and hybridization of analyte from the sample, the unhybridized portions of the sample are washed away. The presence of the analyte of interest, e.g., nucleic acid, hybridized and bound to probe molecules, can then be determined. The fluorophore of the nucleic acid analyte marker is detected by exciting the marker fluorophore at one wavelength and detecting the emitted fluorescent signal with a suitable microarray optical detection and analysis system.

In prior art biomolecule-binding solid support matrices, there is ordinarily a vast excess of binding matrix such as fluorescent nitrocellulose. Such materials contribute significant levels of background fluorescence, and this diminishes their usefulness for microarray-based analysis, especially when only very small quantities of the analyte to be detected are present in the sample. This example demonstrates a comparison of background fluorescence present in a biomolecule-binding matrix of the prior art, such as nitrocellulose membranes deposited on glass slides as taught by Chin (U.S. Pat. No. 6,197,599), with that of spots on a microarray according to the invention under equivalent conditions.

Specifically, an area of a microarray spot of the invention of known diameter is examined for fluorescence at three different excitation and emission wavelengths corresponding to three commonly used fluorophores typically incorporated into nucleic acids in a sample the DNA content of which is to be analyzed. In order to enhance the range of detection of the microarray, particularly at very low levels of analyte, it is most desirable to minimize background fluorescence noise. Spots of equivalent diameter were examined and the values of emitted fluorescence were compared to produce a ratio of gain by dividing the background fluorescence of a spot on a conventional, prior art nitrocellulose-coated slide (e.g., Grace BioLabs) to that emitted by a spot of the same diameter on a microarray of the invention. The data obtained with a Genetic Micro Systems microarray analyzer are shown in Table 1 below:

TABLE 1

| Fluorophore | nm Excitation | nm Emission | Ratios of Gain* | Ratios of Gain+ |
|---|---|---|---|---|
| Cy3 | 550 | 565 | 178 | 61 |
| Cy5 | 650 | 670 | 17 | 22 |
| R-phycoerythrin | 480 | 578 | 178 | 56 |

*The ratios of gain are the ratios of the values of the settings of the detection circuit in order to obtain similar signal for the two types of slides, using an electronic setting reference.
+The ratios of gain in this column were based on use of reference fluorescence of the respective glass slide supports.

The results show that for equivalent size spots using the excitation wavelength for Cy3 fluorophore, a blank spot of a conventional nitrocellulose membrane coated slide of Grace BioLabs has 61 to 178 times the amount of background fluorescence as a spot according to the present invention of equivalent size and biomolecule-binding capacity. Significant improvements by one or two orders of magnitude using microarrays of the invention are also observed for Cy5 and R-phycoerythrin fluorophores. These three fluorophore exemplars are also useful in microarrays for determining protein/protein interactions.

EXAMPLE VI

Comparative Dimensions

In this example, the amount of biomolecule-binding matrix material (e.g., nitrocellulose) required to provide an equivalent binding surface area for the bioanalyte according to the prior art is compared to the amount of such matrix material used to produce colloidal particles according to this invention that have the same binding surface area for contacting the bioanalyte. As is shown below, the reduction in background fluorescence when microarrays according to the invention are used in analytical methods as compared with microarrays of the prior art is due in part to the reduction in thickness (and, consequently, in volume) possible for spots of the same diameter.

With commercially available nitrocellulose-coated glass slides (e.g., Grace Biolabs), a microarray spot of 150 $\mu$m diameter typically has a nitrocellulose thickness of 17 $\mu$m or more. In contrast, an 150 $\mu$m diameter microarray spot prepared from a 25% (v/v) nitrocellulose/aqueous solution according to the invention has thickness of about 0.3 $\mu$m. Therefore, the amount of nitrocellulose present in a typical colloidal microarray spot according to the invention is 0.3/17, or less than 2%, of the nitrocellulose present in a spot on the commercially available nitrocellulose-coated glass slides. Spots having volumes of as little as 100 nl or less (e.g., 50 or 20 nl) are obtainable.

Using a microarray according to the invention, a practitioner can drastically reduce the amount of nitrocellulose and its associated background fluorescence without diminishing the biomolecule probe binding capacity otherwise available. The reduction in thickness of biomolecule-binding matrix agent (e.g., nitrocellulose) is associated necessarily with a corresponding reduction in fluorescence background during, e.g., protein binding detection with fluorophore-labeled antibodies directed against protein analytes bound to the antigen probes. This invention would, therefore, provide greater sensitivity for this assay, particularly for detection of very low levels of protein analyte in a sample. Such very low concentration protein analytes, as may occur in the detection of cancer cell marker proteins in serum samples, may be undetectable with prior art systems of inherently high fluorescence background.

Use

Microarrays according to the invention can easily be adapted for use in a variety of routine diagnostic antibody/antigen-based assays commonly carried out in liquid-based systems in clinical laboratories. For example, blood bank laboratory procedures to determine the presence of antibodies or antigens in the blood of a potential donor could readily be determined. In this case, the antigens of known pathogens, such as surface proteins of the hepatitis virus, can be used as probes in microarray spots, and the donor's serum can be tested for the presence of antibodies to the antigens. Also, the presence of specific pathogens in the donor's blood can be assayed by utilizing antibody probes that are directed against the characteristic antigens of the pathogens of interest. In the same manner, this microassay-based method could be used to diagnose infections as well as monitor the progress of antibiotic or other therapy directed against the pathogens.

In another clinical application, in which antigen/antibody-based assays are used, microarray slides prepared according to this invention can be used to determine levels of therapeutic drugs (e.g., digoxin) or drugs of abuse in a patient's serum. Such assays currently utilize antibody/antigen-based determination techniques. Microarrays of this invention can also be used to detect proteins in a patient's serum, which proteins are diagnostic of disease conditions. For example, CA125 and PSA are protein markers of cancer cells associated with ovarian and prostatic cancer, respectively. Because of the expense associated with commercially available immunoassay kits and procedures to test for these antigens, these tests are most frequently used only after the disease has occurred. With the use of microarrays for these and other cancer antigens (e.g., breast, colon), such tests could be performed readily and with greater facility than current methods. The availability of cancer detection microarray-based assays according to this invention would also facilitate the routine monitoring of cancer therapy to track, e.g., the protein or nucleic acid indicators or markers for various types of cancer. The availability of this efficient system to assay for many cancer markers in an efficient and economic manner could promote earlier detection and early treatment. Thus, microarrays prepared at the point of manufacture as taught herein, instead of being prepared at the user level, have the advantage of providing many diagnostic laboratories with carefully quality controlled-assay components and procedures and thereby provide a common base to compare assay results among thousands of different laboratories.

Microarrays of the current invention are also useful for detecting abnormal serum protein and genetic disorders associated with mutations present in prospective parents, fetuses and newborns for early prediction or detection of certain diseases, such as cystic fibrosis. For this type of use, either protein probe microarrays or DNA probe microarrays can be constructed according to the invention to provide more efficient and less expensive assay methodologies than are commercially available now. Microarrays according to the invention can also be used for diagnosis of immunodeficiency diseases characterized by abnormal antibody profiles of individuals with various immune system disorders.

Microassays of the present invention can also be prepared for use in drug discovery and basic research. In one case, for example, a cell surface receptor or adhesion molecule, the involvement of which is associated with a disease process such as the seminal formation of athrosclerotic plaque such as in hardening of the arteries, can be used as a probe in a microarray. Also, in the same microarray, various closely related probes of comparable but different compositional and structural content could be deposited on the same microarray slide format, for example. Then, solutions containing potential drugs can be incubated with the microarray to allow possible interaction with and/or binding to the drug target of interest. In another embodiment, the potential drugs themselves could be appropriately labeled for detection. Such binding could also be assessed, after the contact incubation, by subsequently exposing the microarray to one or more fluorophore-labeled antibodies. By analyzing the pattern of antibody binding among the various target probe/ microarray spots, one can determine which potential drug candidates specifically bind to the target of interest wherein such binding of a drug candidate would interfere with the subsequent binding of the fluorophore-labeled antibody to the target probe.

It is a fundamental aspect of this invention, with respect to the use of microarrays for clinical diagnostic applications in thousands of different hospital and commercial laboratories, that the analytical system has the highest level of precision and accuracy with minimal laboratory-to-laboratory variations when assaying the same sample for a particular analyte. This invention succeeds in providing such a system by creating a novel combination of the following elements not available in prior art analytical systems, namely: [1] each spot for a given probe and microarray position on many replicate microarrays can be derived from the same lot of liquid colloidal suspension composition at the point of manufacture; [2] secondary microarray preparation steps, such as blocking of the exposed biomolecule-binding sites of the matrix material as well as cross linking the nucleic acid probes within the binding matrix polymer molecules, are performed in bulk at the point of manufacture rather than at the user level; [3] the thickness and amount of probe/liquid colloidal suspension is kept to a minimum required for the assay so as to optimally reduce background interference and maximize assay sensitivity; [4] probe deposition onto the binding matrix is performed on generally micro-spherical surfaces of the matrix in a liquid medium so as to maximize the amount of probe present relative to the amount of potentially assay-interfering binding matrix; [5] an internal standard reference standard, e.g., a dye or chromophore, may be included in the liquid probe/colloidal liquid suspension to provide a convenient means to assess manufacturing quality; [6] the same reference standard as in [5], or a different chromophore as may be preferred, has a defined quantitative relationship to the amount of probe actually deposited on the microarray slide, and this may be used, if necessary, to provide a means for normalization of assay results based on the known quantitative relationship of the probe; and [7] multiple assays for different protein analytes may be performed simultaneously with the microarray of the invention, for example, a single protein probe microarray (e.g., for many different types of cancer cell markers) can be enclosed in a single probe protein reaction chamber and treated sequentially with a single patient serum sample, washed with a single wash reagent and then treated with a single development reagent, which development reagent contains a multiplicity of fluorophore-labeled antibodies and then analysed by a single microarray analysis instrument.

While the present invention has been described in conjunction with a preferred embodiment, one of ordinary skill, after reading the foregoing specification, will be able to effect various changes, substitutions of equivalents, and other alterations to the compositions and methods set forth herein.

What is claimed is:

1. A liquid composition comprising a colloidal suspension of a biomolecule-binding matrix material uniformly dispersed in a liquid, wherein colloidal particles of said matrix material in said colloidal suspension are of a defined particle size of less than about 1 $\mu$m in diameter, and wherein said biomolecule-binding matrix material is selected from the group consisting of nitrocellulose, polyvinyl difluoride and activated nylon;

replicate copies of a biologically active labeled biomolecule, wherein said biomolecules are distributed throughout said colloidal suspension and are bound to said matrix material particles and wherein said biomolecule is selected from the group consisting of a protein, peptide and oligopeptide;

one or more reference dyes distributed throughout said colloidal suspension; and a blocking biomolecule, wherein said blocking biomolecule blocks sites on said biomolecule-binding matrix material not occupied by said biomolecule.

2. The liquid composition of claim 1, wherein the reference dye is a marker for determining the quantity of biomolecule deposited in a spot on a microarray.

3. The liquid composition of claim 1, wherein said particles of matrix material have a diameter of less than 0.5 $\mu$m.

4. The liquid composition of claim 1, wherein said particles of matrix material have a diameter of less than 0.25 $\mu$m.

5. The liquid composition of claim 1 wherein the biomolecule is a protein.

6. The liquid composition of claim 5 wherein the biomolecule-binding matrix material is nitrocellulose.

7. The liquid composition of claim 1, wherein more than one species of biomolecule is distributed throughout said colloidal suspension and bound to said matrix material particles.

8. The liquid composition of claim 7, wherein said more than one species of biomolecule comprise two or more different biomolecule probes.

9. The liquid composition of claim 1, wherein said binding of said biomolecules is covalent binding.

10. The liquid composition of claim 1, wherein said binding of said biomolecules is non-covalent binding.

11. The liquid composition of claim 1, wherein said binding of said biomolecules is electrostatic binding.

12. The liquid composition of claim 1, wherein said binding of said biomolecules is adsorption onto a surface of said matrix material particles.

13. The liquid composition of claim 1, wherein the reference dye is used to track the concentration of matrix material during the preparation of the liquid composition.

* * * * *